(12) United States Patent
Giacomoni

(10) Patent No.: US 7,083,799 B1
(45) Date of Patent: Aug. 1, 2006

(54) NO-SYNTHASE INHIBITORS

(75) Inventor: Paolo Giacomoni, Orsay (FR)

(73) Assignee: L'Oreal, Paris (FR)

( * ) Notice: Subject to any disclaimer, the term of this patent is extended or adjusted under 35 U.S.C. 154(b) by 611 days.

(21) Appl. No.: 08/894,788

(22) PCT Filed: Feb. 26, 1996

(86) PCT No.: PCT/FR96/00296

§ 371 (c)(1), (2), (4) Date: Aug. 27, 1997

(87) PCT Pub. No.: WO96/26711

PCT Pub. Date: Sep. 6, 1996

(30) Foreign Application Priority Data

Feb. 27, 1995 (FR) ................... 95 02267

(51) Int. Cl.
*A61K 8/00* (2006.01)
(52) U.S. Cl. .................... 424/401; 424/70.1
(58) Field of Classification Search ............... 424/401, 424/70.1, 78.03, 78.05; 514/474, 890, 886, 514/887
See application file for complete search history.

(56) References Cited

U.S. PATENT DOCUMENTS

| | | | |
|---|---|---|---|
| 5,137,923 A * | 8/1992 | Philippe et al. | 514/859 |
| 5,358,969 A * | 10/1994 | Williamson et al. | 514/632 |
| 5,360,925 A | 11/1994 | Chabrier de Lassauniere et al. | |
| 5,449,688 A * | 9/1995 | Wahl et al. | 514/546 |
| 5,468,476 A * | 11/1995 | Ahluwalia et al. | 424/73 |
| 5,476,661 A * | 12/1995 | Pillai et al. | 424/401 |
| 5,716,625 A * | 2/1998 | Hahn et al. | 424/401 |
| 5,847,003 A * | 12/1998 | Ptchelintsev et al. | 514/532 |
| 5,951,990 A * | 9/1999 | Ptchelintsev | 424/401 |

FOREIGN PATENT DOCUMENTS

| | | |
|---|---|---|
| EP | 0 096 521 | 12/1983 |
| EP | 0 249 736 | 12/1987 |
| EP | 0 366 990 | 5/1990 |
| EP | 0 413 528 | 2/1991 |
| EP | 0 630 649 | 12/1994 |
| GB | 2 240 041 A | 7/1991 |
| GB | 2 263 111 | 7/1993 |
| WO | WO 93/24126 | 12/1993 |
| WO | WO 95/13805 | 5/1995 |
| WO | WO 95/24884 | 9/1995 |

OTHER PUBLICATIONS

Wilhelm et al, Surfactant-induced skin irritation and skin repair:evaluation of a cumulative human irritation model by noninvasive techniques, Journal of American Academy of Dermatology, 31 (6), 981-987, 1994.*

English Language Derwent Abstract entitled "Cosmetics Used for Skin Whitening," abstract No. 95-355173.

Armando Ialenti et al., "Modulation of acute inflammation by endogenous nitric oxide," *European Journal of Pharmacology*, 211 (1992) pp. 177-182.

Unofficial translated copy of Opposition to European Patent No. 0 812 184 (EP counterpart of U.S. Appl. No. 08/894,788.

* cited by examiner

*Primary Examiner*—Thurman K. Page
*Assistant Examiner*—Lakshmi Channavajjala
(74) *Attorney, Agent, or Firm*—Finnegan, Henderson, Farabow, Garrett & Dunner L.L.P.

(57) ABSTRACT

The use of an effective amount of at least one nitric oxide synthase inhibitor in a cosmetic composition or for making a pharmaceutical composition is disclosed, said inhibitor or pharmaceutical composition being intended to reduce the skin irritant effect of topically applied cosmetic or pharmaceutical substances. A cosmetic or pharmaceutical composition containing an effective amount of at least one nitric oxide synthase inhibitor, and a cosmetic treatment method using said cosmetic composition, are also disclosed.

34 Claims, No Drawings

NO-SYNTHASE INHIBITORS

The present invention relates to a use of an effective quantity of at least one NO-synthase inhibitor in a cosmetic composition or for the manufacture of a pharmaceutical composition, this inhibitor or the pharmaceutical composition being intended to reduce the cutaneous irritant effect of products used topically in the cosmetic or pharmaceutical field.

It also relates to a cosmetic or pharmaceutical composition comprising an effective quantity of at least one NO-synthase inhibitor and a process of cosmetic treatment using the cosmetic composition according to the invention.

Within the framework of the present invention, the cutaneous irritant effect is a response of the skin which is most often manifested by blotches, pain or pricking, this response being generated by chemical products of natural or synthetic origin which are topically applied to the skin. This irritation is accompanied by impairment of the epithelial structure and/or function which is directly linked to the effect of the product having an irritant character.

Thus, the disruptions induced by a product having an irritant character are followed by a response of the skin which is intense to a greater or lesser degree aimed at restoring the homeostatic equilibrium which is broken or to repair the damages caused. This response may be infraclinical, that is to say without obvious inflammatory reaction to the naked eye. However, the reaction which is intense to a greater or lesser degree remains the most usual tissue response to aggression caused by an irritant product and the most disturbing for the user of this product having an irritant character.

When the product having an irritant character reaches the skin, it can react with certain pre-existing substances in the cells and the tissues and/or liberate intracellular substances. These liberated substances may, in turn, become active on other targets in the epithelium or the dermis. Thus, begins the cascade of reactions which, through the recruitment of blood cells and the substances which they liberate, give rise to the irritant process which is characterized mainly by irritation of the skin. This process is manifested in particular in various degrees, depending mainly on the quality and/or quantity of the product applied and/or the user of this product, by dysaesthetic sensations (inflammation, burning sensations, itching or pruritus, sensations of pricking, of twitching and the like), by blotches and/or by an oedema.

These products having an irritant character may be used in cosmetic or pharmaceutical, and more particularly dermatological, compositions quite obviously for other effects. Thus, they are generally used as active agents, surfactants, preservatives, perfumes, solvents or propellents for the said compositions.

However, because of their irritant character, these products are generally used in very low doses. The use of these products in small quantities may then prove to be of little advantage compared with the use of other products which are less active but less or not irritant and which are therefore used in a larger quantity.

Consequently, there is a need in the cosmetic and pharmaceutical field to find a means allowing these products to be used, without the latter exhibiting an irritant character which can be criticized by the user.

Now, the Applicant has discovered that the NO-synthase inhibitors make it possible to limit, or even suppress, the irritant character of these products.

Thus, the subject of the present invention is the use of an effective quantity of at least one NO-synthase inhibitor in a cosmetic composition or for the manufacture of a pharmaceutical composition, this inhibitor or the pharmaceutical composition being intended to reduce the cutaneous irritant effect of products topically used in the cosmetic or pharmaceutical field.

The cosmetic or pharmaceutical composition comprising the NO-synthase inhibitor may comprise or otherwise the product capable of causing a cutaneous irritation.

In the case where these compounds exist in the same composition, the present invention also relates to a composition for topical, cosmetic or pharmaceutical use, characterized in that it comprises, in a cosmetically or pharmaceutically acceptable medium, an effective quantity of at least one NO-synthase inhibitor and at least one product capable of causing cutaneous irritation.

The pharmaceutical composition is preferably a dermatological composition.

The present invention also relates to a process of cosmetic treatment, characterized in that it uses the cosmetic composition according to the invention.

The effective quantity of at least one NO-synthase inhibitor according to the invention is a sufficient quantity of at least one NO-synthase inhibitor so that the cutaneous irritant effect decreases or even disappears. Thus, this quantity is variable depending on the quantity and the nature of the product having an irritant character which is applied. However, by way of illustration, a composition according to the invention may comprise at least one NO-synthase inhibitor at a concentration by weight of between $10^{-6}$% and 10% of the total weight of the composition and preferably between $10^{-4}$% and 1% of the total weight of the composition.

In the composition according to the invention, the quantity of the product capable of causing a cutaneous irritation may therefore correspond to a quantity which is sufficient to cause a cutaneous irritation if it was used alone (without the NO-synthase inhibitor).

Numerous topically applied products exhibit an irritant character, especially for people (users) with easily irritable skins.

Thus, even the products which are considered to be inert in a cosmetic or pharmaceutical, more particularly dermatological, composition may exhibit an irritant character when they are applied to the skin, the scalp, the nails or the mucous membranes, such as in particular preservatives, surfactants, perfumes, solvents or propellents.

Accordingly, products considered as active agents in cosmetic or pharmaceutical compositions may exhibit an irritant character when they are applied to the skin, the scalp, the nails or the mucous membranes, it is possible to speak of a secondary irritant effect, such as especially some sunscreens, α-hydroxy acids (glycol, lactic, malic, citric, tartaric, mandelic), β-hydroxy acids (salicylic acid and its derivatives), α-keto acids, β-keto acids, retinoids (retinol and its esters, retinal, retinoic acid and its derivatives, retinoids, especially those described in the documents FR-A-2,570,377, EP-A-199,636, EP-A-325,540, EP-A-402,072), anthralins (dioxyanthranol), anthranoids (for example those described in the document EP-A-319,028), peroxides (especially benzoyl peroxide), minoxidil and its derivatives, lithium salts, antiproliferative agents, such as 5-fluorouracyl or methotrexate, some vitamins, such as vitamin D and its derivatives, vitamin B9 and its derivatives, hair dyes or colorants (para-phenylenediamine and its derivatives, aminophenols), perfuming alcoholic solutions (perfumes, toilet water, aftershave, deodorants), antiperspirants (some aluminium salts), depilatory or permanent waving active agents (thiols), depigmenting agents (hydroquinone), capsaicin, antilouse active agents (pyrethrin), ionic and nonionic detergent agents and propigmenting agents (dihydroxyacetone, psoralens and methylangecilins).

Among these products with a secondary irritant effect, the invention relates more particularly to retinoids.

Among the retinoids, there may be mentioned more particularly all-trans-retinoic acid, 13-cis-retinoic acid, 2-(5,6,7,8-tetrahydro-5,5,8,8-tetra-methyl-2-naphthyl)-6-benzo[b]thiophenecarboxylic acid, 6-[3-(1-adamantyl)-4-methoxyphenyl]-2-naphthanoic acid sold under the name Adapalène™ by the company Galderma, Tazarotène™, having the generic chemical name, 6-[(3,4-dihydro-4,4-dimethyl-2H-1-benzothiopyran-6-yl)ethylnyl]-3-pyridinecarboxylic acid ethyl ester, sold by the company Allergan.

Among the vitamin D and its derivatives, there may be mentioned more particularly vitamin $D_3$, vitamin $D_2$, 1,25-diOH vitamin $D_3$ (calcitriol), calcipotriol, 1,24-diOH vitamin $D_3$ (such as tacalcitol), 24,25-diOH vitamin $D_3$, 1-OH vitamin $D_2$, 1,24-diOH vitamin $D_2$.

Among the salicylic acid derivatives, there may be mentioned more particularly 5-n-octanoyl-salicylic acid and 5-n-dodecanoylsalicylic acid or their esters.

The nitrogen monoxide (NO) is enzymatically generated by L-arginine, the enzyme being called NO-synthase.

The NO-synthase inhibitors are, according to the invention, products which make it possible in situ, in man, to partially or even completely inhibit the synthesis of nitrogen monoxide (NO).

This enzyme exists in two forms, the constitutive form and the inducible form (Medecine/Sciences, 1992, 8, pp. 843–845). Among the inhibitors, use of the inhibitors of constitutive NO-synthase is preferred, that is to say the inhibitors which inhibit the constitutive NO-synthase equally or more compared with the inducible NO-synthase. The tests to identify the inhibitors of constitutive or inducible NO-synthase are described in particular in U.S. Pat. No. 5,132,453.

Among these inhibitors of constitutive NO-synthase, the inhibitors of endothelial NO-synthase are preferred.

Indeed, it seems, without wishing to be tied to any theory of the invention, that the reduction in irritation observed in the present invention is due mainly to the inhibition of the constitutive NO-synthases, and more particularly to the inhibition of the NO-synthase of the endothelial cells.

Thus, among these inhibitors of the constitutive NO-synthase, there may be mentioned more particularly $N^G$-monomethyl-L-arginine (NMMA), the methyl ester of $N^G$-nitro-L-arginine (NAME), $N^G$-nitro-L-arginine (NNA), $N^G$-amino-L-arginine (NAA), $N^G,N^G$-dimethylarginine (asymmetric dimethylarginine, called ADMA).

NMMA, NAME, NNA and ADMA are preferably used.

The inhibitors of NO-synthase may be used alone or as a mixture.

The inhibitors of NO-synthase may be used both for preventive and curative purposes.

The present invention has in particular the advantage of being able to increase the quantity of active agents having an irritant character in cosmetic or pharmaceutical compositions compared with the quantity normally used, for an enhanced efficacy of the said active agents. Thus, the hydroxy acids may be used up to 50% of the weight of the composition or the retinoids up to 5%, without any inconvenience for the user.

The NO-synthase inhibitor(s) may be used by the enteral, parenteral or topical route.

By the topical route, direct application to the skin, the scalp, the nails or the mucous membranes is preferred.

The compositions according to the invention may be provided in any galenic form. These compositions are prepared according to the customary methods.

A cosmetically or dermatologically acceptable medium generally corresponds to a medium which is compatible with the skin, the scalp, the nails or the mucous membranes. The composition comprising the NO-synthase inhibitor may therefore be applied to the face, the neck, the hair and the nails, or any other cutaneous zone of the body (axillary or submammary regions, the elbow bend and the like).

By the topical route, the compositions according to the invention are provided especially in the form of aqueous, aqueous-alcoholic or oily solutions, of dispersions of the lotion or serum type, of anhydrous or lipophilic gels, of emulsions of liquid or semi-liquid consistency of the milk type, obtained by dispersion of a fatty phase in an aqueous phase (O/W) or conversely (W/o), or of suspensions or emulsions of soft, semi-solid or solid consistency of the cream or gel type, or of microemulsions, microcapsules, microparticles or vesicular dispersions of the ionic and/or nonionic type. These compositions are prepared according to the customary methods.

By the enteral route, the compositions according to the invention may be provided in the form of tablets, gelatin capsules, sugar-coated tablets, syrups, suspensions, solutions, powders, granules, emulsions, microspheres or nanospheres or lipid or polymeric vesicles which allow a controlled release.

By the parenteral route, the compositions may be provided in the form of solutions or suspensions for infusion or injection.

They may also be used on the scalp in the form of aqueous, alcoholic or aqueous-alcoholic solutions, or in the form of creams, gels, emulsions, foams or in the form of compositions for an aerosol also containing a pressurized propelling agent.

The quantities of the various constituents of the compositions according to the invention are those conventionally used in the fields considered.

These compositions constitute in particular shaving foams, cleansing, protective, treatment or care creams for the face, for the hands, for the feet, for the large anatomical folds or for the body, (for example day creams, night creams, make-up removing creams, foundation creams, antisun creams), fluid foundations, make-up removing milks, protective or care body milks, antisun or better still after-sun milks, skin care lotions, gels or foams, such as lotions for cleansing or disinfection, antisun lotions, artificial tanning lotions, bath compositions, deodorant compositions containing a bactericidal agent, aftershave gels or lotions, depilatory creams, compositions against insect bites, antipain compositions or compositions for treating certain skin diseases such as those mentioned above.

The compositions according to the invention may also consist of solid preparations constituting cleansing soaps or cakes.

The compositions may also be packaged in the form of an aerosol composition also containing a pressurized propelling agent.

The NO-synthase inhibitors may also be incorporated into various compositions for hair care or treatments, especially shampoos which are optionally antiparasitic, hair setting lotions, treatment lotions, hair styling creams or gels, dyeing (especially oxidation dyeing) compositions optionally in the form of dyeing shampoos, restructuring lotions for the hair, permanent waving compositions (especially compositions for the first stage of a permanent waving), lotions or gels against hair loss, and the like.

The compositions of the invention may also be for dentibuccal use, for example a toothpaste or a mouthwash. In this case, the compositions may contain customary adjuvants and additives for compositions for buccal use and especially surfactants, thickening agents, humectants, polishing agents such as silica, various active ingredients such as fluorides, in particular sodium fluoride, and optionally sweetening agents such as sodium saccharinate.

When the composition of the invention is an emulsion, the proportion of fatty phase may range from 5% to 80% by weight, and preferably from 5% to 50% by weight relative to the total weight of the composition. The oils, emulsifiers and coemulsifiers used in the composition in the form of an emulsion are chosen from those conventionally used in the cosmetic and pharmaceutical fields. The emulsifier and the coemulsifier are present in the composition in a proportion ranging from 0.3% to 30% by weight, and preferably from 0.5 to 30% or better still from 0.5 to 20% by weight relative to the total weight of the composition. The emulsion may, in addition, contain lipid vesicles.

When the composition of the invention is an oily gel or a solution, the fatty phase may represent more than 90% of the total weight of the composition.

In a known manner, the composition of the invention may also contain adjuvants common in the cosmetic or pharmaceutical field, such as hydrophilic or lipophilic gelling agents, hydrophilic or lipophilic active agents, preservatives, antioxidants, solvents, perfumes, fillers, screening agents, bactericides, odour absorbers and colouring matter. The quantities of these various adjuvants are those conventionally used in the cosmetic or pharmaceutical field, and for example from 0.01% to 10% of the total weight of the composition. These adjuvants, depending on their nature, may be introduced into the fatty phase, into the aqueous phase and/or into the lipid spherules.

As oils which can be used in the invention, there may be mentioned mineral oils (petroleum jelly), vegetable oils (liquid fraction of shea butter, sunflower oil), animal oils (perhydrosqualene), synthetic oils (Purcellin oil), silicone oils (cyclomethicone) and fluorinated oils (perfluoropolyethers). There may also be used, as fatty substances, fatty alcohols, fatty acids (stearic acid), waxes (paraffin, carnauba, beeswax).

As emulsifiers which can be used in the invention, there may be mentioned for example glycerol stearate, polysorbate 60 and the PEG-6/PEG-32/Glycol Stearate mixture sold under the name Tefose® 63 by the company Gattefosse.

As solvents which can be used in the invention, there may be mentioned the lower alcohols, especially ethanol and isopropanol, propyleneglycol.

As hydrophilic gelling agents, there may be mentioned the carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, there may be mentioned modified clays such as bentones, metal salts of fatty acids such as aluminium stearates and hydrophobic silica, or ethylcellulose, polyethylene.

As hydrophilic active agents, there may be used proteins or protein hydrolysates, amino acids, polyols, urea, allantoin, sugars and sugar derivatives, water-soluble vitamins, starch and plant extracts, especially those of aloe vera.

As lipophilic active agents, there may be used retinol (vitamin A) and its derivatives, tocopherol (vitamin E) and its derivatives, essential fatty acids, ceramides, essential oils.

The NO-synthase inhibitors may, inter alia, be combined with active agents intended especially for the prevention and/or treatment of skin conditions. Among these active agents, there may be mentioned, by way of example:

agents modulating skin differentiation and/or proliferation and/or pigmentation such as especially retinoids, vitamin D and its derivatives, oestrogens such as estradiol, kojic acid or hydroquinone;

antibacterials such as clindamycin phosphate, erythromycin or antibiotics of the tetracycline class;

antiparasitic agents, in particular metronidazole, crotamiton or pyrethrinoids;

antifungal agents, in particular the compounds belonging to the imidazole class such as econazole, ketoconazole or miconazole or their salts, the polyene compounds, such as amphotericin B, the compounds of the allylamine family, such as terbinafine, or octopirox;

steroidal anti-inflammatory agents such as hydrocortisone, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;

anaesthetic agents such as lidocaine hydrochloride and its derivatives;

antipruriginous agents such as thenaldine, trimeprazine or cyproheptadine;

antiviral agents such as acyclovir;

keratolytic agents such as alpha- and beta-hydroxycarboxylic or beta-ketocarboxylic acids, their salts, amides or esters and more particularly alpha-hydroxy acids such as glycolic acid, lactic acid, tartaric acid, citric acid and, in general, fruit acids and beta-hydroxy acids such as salicylic acid and its derivatives, especially alkylated derivatives, such as 5-n-octanoylsalicylic acid;

anti-free radical agents, such as alpha-tocopherol or its esters, superoxide dismutases, certain metal chelators or ascorbic acid and its esters;

antiseborrhoeic agents such as progesterone;

antidandruff agents such as octopirox or zinc pyrithione;

anti-acne agents such as retinoic acid or benzoyl peroxide.

Of course persons skilled in the art will be careful to choose the possible compound(s) present in the composition according to the invention so that the properties intrinsically linked to the present invention are not, or not substantially, altered.

The pharmaceutical compositions according to the invention are particularly suitable in the following fields of treatment, these treatments being particularly appropriate when these compositions comprise retinoids:

1) for treating dermatological conditions linked to a keratinization disorder related to differentiation and proliferation especially to treat acne vulgaris, comedo-type acne, polymorphic acne, rosacea, nodulocystic acne, acne conglobata, senile acne, secondary acne such as solar acne, acne medicamentosa or occupational acne, 2) for treating other types of keratinization disorders, especially ichthyosis, ichthyosiform states, Darier's disease, keratosis palmaris et plantaris, leukoplasia and leukoplasiform states, cutaneous or mucosal (buccal) lichen, 3) for treating other dermatological conditions linked to a keratinization disorder with an inflammatory and/or immunoallergic component, and especially all the forms of psoriasis, whether cutaneous, mucosal or ungual, and even psoriatic rheumatism, or cutaneous atopy, such as eczema or respiratory atopy or gingival hypertrophy; the compounds may also be used in certain inflammatory conditions which do not exhibit keratinization disorder, 4) for treating any dermal or epidermal proliferations whether benign or malignant, whether of viral origin or not, such as verruca vulgaris, verruca plana and epidermodysplasia verruciformis, oral or florid papillomatoses and proliferations which may be induced by ultraviolet radiation especially in the case of baso- and spinocellular epithelioma, 5) for treating other dermatological disorders such as bullous dermatoses and collagen diseases, 6) for treating certain ophthalmological disorders, especially corneopathies, 7) for repairing or combating skin ageing, whether photoinduced or chronologic, or for reducing pigmentations and actinic keratoses, or any pathologies associated with chronologic or actinic ageing, 8) for preventing or curing the stigmas of epidermal and/or dermal atrophy induced by local or systemic corticosteroids, or any other form of cutaneous atrophy, 9) for preventing or treating cicatrization disorders or preventing or repairing vibices, 10) for combating disorders of the sebaceous function, such as hyperseborrhoea of acne or simple seborrhoea, 11) in the treatment or prevention of cancerous or precancerous states, 12) in the treatment of inflammatory conditions such as arthritis, 13) in the treatment of any condition of viral origin at the cutaneous level or in general, 14) in the prevention or treatment of alopecia, 15) in the treatment of dermatological or general conditions with an immunological component, 16) in the treatment of conditions of the cardiovascular system, such as arteriosclerosis.

The subject of the present invention is, in addition, a process of cosmetic treatment, characterized in that it uses the cosmetic composition according to the invention.

Preferably, the process of cosmetic treatment consists in applying to the skin, the scalp and/or the mucuous membranes a composition as described above.

The process of cosmetic treatment of the invention can be carried out in particular by applying the hygiene or cosmetic compositions as defined above, according to the usual technique for using these compositions. For example: application of creams, gels, sera, lotions, make-up removing milks or after-sun compositions to the skin or to dry hair, application of a hair lotion to wet hair, of shampoo or application of toothpaste to the gums.

In the cosmetic field, the compositions according to the invention are suitable, depending on the active agents contained in this composition, in particular in body and hair hygiene and especially for the treatment of skins which tend to have acne, for hair regrowth, against hair loss, for combating the greasy appearance of the skin or the hair, in protection against the harmful aspects of the sun or in the treatment of physiologically dry skins, for preventing and/or for combating photo-induced or chronologic ageing.

Several examples for obtaining active compounds of formula (I) according to the invention, as well as various concrete formulations based on such compounds will now be given by way of illustration and with no limitation being implied.

EXAMPLE 1

The aim of this example is to demonstrate the oral anti-irritant activity in vivo of the methyl ester of $N^G$-nitro-L-arginine used for curative purposes.

The test used to evaluate this activity is that of mouse ear oedema (Balb/C mouse) induced by topical application of 0.01% by weight of 2-(5,6,7,8-tetrahydro-5,5,8,8-tetramethyl-2-naphthyl)-6-benzo[b]thiophenecarboxylic acid. According to this model, the response to a topical application of 2-(5,6,7,8-tetrahydro-5,5,8,8-tetramethyl-2-naphthyl)-6-benzo[b]thiophenecarboxylic acid to the ear results in an increase in the thickness of the ear which is maximum 5 days after the application. This increase in the thickness of the mouse ear appears to be due to an increase in the thickness of the epidermis and to the appearance of a dermal oedema. This response can therefore be easily measured with the aid of an apparatus, such as the oditest.

The exact operating procedure is the following: 10 mice are first treated with the active product having an irritant character by topically applying to one of their ears at time t=0 with 20 µl of an acetone solution containing 0.01% by weight of 2-(5,6,7,8-tetrahydro-5,5,8,8-tetramethyl-2-naphthyl)-6-benzo[b]thiophenecarboxylic acid. 5 (=group 2) of the 10 mice thus treated are made to ingest orally $N^G$-nitro-L-arginine methyl ester in drinking water from t=0 and once per day for 11 days ($N^G$-nitro-L-arginine methyl ester concentration of 1 mg/ml, that is to say 170±40 mg/kg per day). The 5 mice which did not ingest the $N^G$-nitro-L-arginine methyl ester constitute group 1. The oedematous response is quantified by measurement of the thickness of the ear. The results are then expressed as % increase in the thickness of the mouse ear compared to the increase in thickness observed on the other ear which, for its part, was treated (under the same conditions as above) with only an acetone solution without active agent (control or reference ear).

The results obtained are as follows:

After 5 days of treatment, the increase in the thickness of the mouse ear is at its maximum (100%) for group 1 and is 70% for group 2.

The above results clearly demonstrate a 30% inhibition of the ear oedema for the mice treated with this NO-synthase inhibitor.

Furthermore, no sign of toxicity was observed and the change in weight was not modified in the mice treated with this inhibitor.

EXAMPLE 2

The aim of this example is to demonstrate the topical anti-irritant activity in vivo of $N^G,N^G$-dimethylarginine administered for preventive purposes.

The test used to evaluate this activity is the same as that used in Example 1.

The exact operating procedure is the following: 5 mice are first treated with a gel comprising, as sole active agent, 1% by weight of $N^G,N^G$-dimethylarginine by one topical application per day to one of their ears for 4 days. No increase in the thickness of the ear of the mice thus treated is observed. Next, there is topically applied to the ear of these 5 mice previously treated with $N^G,N^G$-dimethylarginine (group A) and to the ear of 5 untreated mice (group B), at time t=0, 20 µl of an acetone solution comprising 0.01% by weight of 2-(5,6,7,8-tetrahydro-5,5,8,8-tetramethyl-2-naphthyl)-6-benzo[b]thiophenecarboxylic acid. The oedematous response is quantified by measurement of the thickness of the ear. The results are then expressed as % increase in the thickness of the mouse ear compared with the increase in thickness observed on the other ear which, for its part, was treated (under the same conditions as above), with only an acetone solution without active agent (control or reference ear and oedema).

By comparing groups A and B, the results obtained are the following:

$N^G,N^G$-dimethylarginine applied topically once per day for 4 days before the application of the product having an irritant character (2-(5,6,7,8-tetrahydro-5,5,8,8-tetramethyl-2-naphthyl)-6-benzo[b]thiophenecarboxylic acid) reduces by 24% the amplitude and by 50% the area under the curve of the response induced by the product having an irritant character (the curve corresponding to the thickness of the ear as a function of the days for the reading).

EXAMPLE 3

The aim of this example is to demonstrate the topical anti-irritant activity in vivo of $N^G$-monomethyl-L-arginine (L-NMMA) used for curative purposes.

The test used to evaluate this activity is the same as that used in Example 1.

The exact operating procedure is the following: 10 mice are first treated with the active product having an irritant character by topically applying to one of their ears at time t=0 with 20 µl of an acetone solution containing 0.01% by weight of 2-(5,6,7,8-tetrahydro-5,5,8,8-tetramethyl-2-naphthyl)-6-benzo[b]thiophenecarboxylic acid. A gel comprising 1% by weight of L-NMMA is topically applied to 5 (=group 2) of the 10 mice thus treated 6 hours after the application of the product having an irritant character, once per day for 5 days. The 5 mice which were not treated with L-NMMA constitute group 1. The oedematous response is quantified by measurement of the thickness of the ear. The results are then expressed as % increase in the thickness of the mouse ear compared to the increase in thickness observed on the other ear which, for its part, was treated (under the same conditions as above) with only an acetone solution without active agent (control or reference ear).

The results obtained are as follows:

After 5 days of treatment, the increase in the thickness of the mouse ear is at its maximum (100%) for group 1 and is 72% for group 2.

The results clearly demonstrate a 28% inhibition of the ear oedema for the mice treated with this NO-synthase inhibitor.

L-NMMA reduces by 51% the area under the curve of the response induced by the product having an irritant character (the curve corresponding to the thickness of the ear as a function of the days for the reading).

If the same treatment is carried out by applying, in place of L-NMMA, 1% or 5% betaine or 1% $N^G,N^G$-dimethyl-L-arginine (symmetric dimethyl-L-arginine, called SDMA), a 9, 16 and 7% inhibition of the oedema of the ear is observed, respectively, for the mice treated with these products which are not NO-synthase inhibitors (see especially for SDMA: The Lancet, Vol. 339: 572–575). A 24, 13 and 27% reduction in the area under the curve of the response induced by the product having an irritant character is also observed respectively (the curve corresponding to the thickness of the ear as a function of the days for the reading).

EXAMPLE 4

Compositions in accordance with the invention, provided in the form of a lotion, a gel and a cream for topical use, are illustrated here.

| | % by weight |
|---|---|
| LOTION | |
| Disodium EDTA | 0.1 |
| Poloxamer 182 | 0.2 |
| Water | qs 100 |
| Ethoxydiglycol | 5 |
| $N^G, N^G$-dimethylarginine | 1 |
| GEL | |
| Disodium EDTA | 0.1 |
| Poloxamer 182 | 0.2 |
| Water | qs 100 |
| Sepigel 305 sold by Seppic | 3 |
| Ethoxydiglycol | 5 |
| $N^G, N^G$-dimethylarginine | 1 |
| CREAM | |
| Disodium EDTA | 0.1 |
| Poloxamer 182 | 0.2 |
| Water | qs 100 |
| Preservatives | 0.3 |
| Sepigel 305 sold by Seppic | 3 |
| Apricot kernel oil | 10 |
| Cyclomethicone | 5 |
| Ethoxydiglycol | 5 |
| Methyl ester of $N^G$-nitro-L-arginine | 1 |
| CREAM oil-in-water emulsion | |
| $N^G$-monomethyl-L-arginine (NMMA) | $10^{-2}$ |
| Glycerol stearate | 2.00 |
| Polysorbate 60 (Tween 60 sold by the company ICI) | 1.00 |
| Stearic acid | 1.40 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.50 |
| Preservative | 0.30 |
| Water | qs 100 |
| LOTION | |
| Adapalène ™ | 0.010 g |
| $N^G$-monomethyl-L-arginine (NMMA) | 0.100 g |
| Polyethyleneglycol (PEG 400) | 69.890 g |
| Ethanol 95% | 30.000 g |

What is claimed is:

1. A cosmetic or pharmaceutical composition, said composition comprising,
   in a cosmetically or pharmaceutically acceptable medium, at least one cosmetic
   or pharmaceutical product capable of causing a cutaneous irritant effect, and at least one topically applied nitric oxide synthase inhibitor,
      wherein said at least one topically applied nitric oxide synthase inhibitor is present in an amount effective to reduce the cutaneous irritant effect of said at least one cosmetic or pharmaceutical product.

2. A composition according to claim 1, wherein said pharmaceutical composition is a dermatological composition.

3. A composition according to claim 1, wherein said at least one nitric oxide synthase inhibitor is present in a concentration ranging from $10^{-6}$% to 10% by weight relative to the total weight of the composition.

4. A composition according to claim 3, wherein said at least one nitric oxide synthase inhibitor is present in a concentration ranging from $10^{-4}$% to 1% by weight relative to the total weight of the composition.

5. A composition according to claim 1, wherein said at least one cosmetic or pharmaceutical product is a preservative, a surfactant, a perfume, a solvent or a propellant.

6. A composition according to claim 5, wherein said at least one cosmetic or pharmaceutical product is a sunscreen, an α-hydroxy acid, a β-hydroxy acid, an α-keto acid, a β-keto acid, a retinoid, an anthralin, an anthranoid, a peroxide, minoxidil or one of its derivatives, a lithium salt, an antiproliferative agent, vitamin D or one of its derivatives, vitamin B9 or one of its derivatives, a hair dye, a hair colorant, capsaicin, a perfuming alcoholic solution, an antiperspirant, a depilatory waving active agent, a permanent waving active agent, a depigmenting agent, an antilouse active agent, a detergent or a propigmenting agent.

7. A composition according to claim 6, wherein said β-hydroxy acid is salicylic acid or one of its derivatives.

8. A composition according to claim 6, wherein said at least one cosmetic or pharmaceutical product is a retinoid.

9. A composition according to claim 6, wherein said vitamin D or one of its derivatives is vitamin $D_3$, vitamin $D_2$, 1,25-diOH vitamin $D_3$, calcipotriol, 1,24-diOH vitamin $D_3$, 24,25-diOH vitamin $D_3$, 1-OH vitamin $D_2$, or 1,24-diOH vitamin $D_2$.

10. A composition according to claim 9, wherein said 1,24-diOH vitamin $D_3$ is tacalcitol.

11. A composition according to claim 7, wherein said salicylic acid derivative is 5-n-octanoylsalicylic acid, 5-n-dodecanoylsalicylic acid or one of their esters.

12. A composition according to claim 1, wherein said at least one nitric oxide synthase inhibitor is an inhibitor of constitutive nitric oxide synthase.

13. A composition according to claim 12, wherein said inhibitor of constitutive nitric oxide synthase is an inhibitor of endothelial nitric oxide synthase.

14. A composition according to claim 12, wherein said at least one nitric oxide synthase inhibitor is $N^G$-monomethyl-L-arginine, the methyl ester of $N^G$-nitro-L-arginine, $N^G$-nitro-L-arginine, $N^G$-amino-L-arginine, or $N^G,N^G$-dimethylarginine.

15. A composition according to claim 14, wherein said at least one nitric oxide synthase inhibitor is the methyl ester of $N^G$-nitro-L-arginine, $N^G,N^G$-dimethylarginine, $N^G$-nitro-L-arginine or $N^G$-monomethyl-L-arginine.

16. A composition according to claim 1, wherein said composition is formulated in order to be applied topically to the skin, the scalp or the mucous membranes.

17. A method of reducing the cutaneous irritant effect of a topically applied cosmetic or pharmaceutical composition containing at least one cosmetic or pharmaceutical product capable of having an irritant character on the skin, the scalp, the nails or the mucous membranes, said method comprising applying said cosmetic or pharmaceutical product to said skin, scalp, nails or mucous membranes, wherein said cosmetic or pharmaceutical composition further comprises at least one nitric oxide synthase inhibitor in an amount effective to reduce the cutaneous irritant effect of said at least one cosmetic or pharmaceutical product.

18. A method according to claim 17, wherein said at least one nitric oxide synthase inhibitor is present in a concentration ranging from $10^{-6}$% to 10% by weight relative to the total weight of the composition.

19. A method according to claim 18, wherein said at least one nitric oxide synthase inhibitor is present in a concentration ranging from $10^{-4}$% to 1% by weight relative to the total weight of the composition.

20. A method according to claim 19, wherein said at least one cosmetic or pharmaceutical product is a preservative, a surfactant, a perfume, a solvent or a propellant.

21. A method according to claim 17, wherein said at least one cosmetic or pharmaceutical product is a sunscreen, an α-hydroxy acid, a β-hydroxy acid, an α-keto acid, β-keto acid, a retinoid, an anthralin, an anthranoid, a peroxide, minoxidil or one of its derivatives, a lithium salt, an antiproliferative agent, vitamin D or one of its derivatives, vitamin B9: or one of its derivatives, a hair dye, a hair colorant, capsaicin, a perfuming alcoholic solution, an antiperspirant, a depilatory waving active agent, a permanent waving active agent, a depigmenting agent, an antilouse alive agent, a detergent or a propigmenting agent.

22. A method according to claim 21, wherein said β-hydroxy acid is salicylic acid or one of its derivatives.

23. A method according to claim 21, wherein said at least one cosmetic or pharmaceutical product is a retinoid.

24. A method according to claim 21, wherein said vitamin D or one of its derivatives is vitamin $D_3$, vitamin $D_2$, 1,25-diOH vitamin $D_3$, calcipotriol, 1,24-diOH vitamin $D_3$, 24,25-diOH vitamin $D_3$, 1-OH vitamin $D_2$ or 1,24-diOH vitamin $D_2$.

25. A method according to claim 24, wherein said 1,24-diOH vitamin $D_3$ is tacalcitol.

26. A method according to claim 22, wherein said salicylic acid derivative is 5-n-octanoylsalicylic acid, 5-n-dodecanoylsalicylic acid or one of their esters.

27. A method according to claim 17, wherein said at least one nitric oxide synthase inhibitor is an inhibitor of constitutive nitric oxide synthase.

28. A method according to claim 27, wherein said inhibitor of constitutive nitric oxide synthase is an inhibitor of endothelial nitric oxide synthase.

29. A method according to claim 27, wherein said at least one nitric oxide synthase inhibitor is $N^G$-monomethyl-L-arginine, the methyl ester of $N^G$-nitro-L-arginine, $N^G$-nitro-L-arginine, $N^G$-amino-L-arginine, or $N^G,N^G$-dimethylarginine.

30. A method according to claim 29, wherein said at least one nitric oxide synthase inhibitor is the methyl ester of $N^G$-nitro-L-arginine, $N^G,N^G$-dimethylarginine, $N^G$-nitro-L-arginine or $N^G$-monomethyl-L-arginine.

31. A process for the cosmetic treatment of the skin, the scalp, the nails or the mucous membranes, said process comprising applying a cosmetic composition according to claim 1 to said skin, scalp, nails or mucous membranes.

32. A process for the pharmaceutical treatment of the skin, the scalp, the nails or the mucous membranes, said process comprising applying a pharmaceutical composition according to claim 1 to said skin, scalp, nails or mucous membranes.

33. A composition according to claim 8, wherein said retinoid is all-trans-retinoic acid, 13-cis-retinoic acid, 2-(5,6,7,8-tetrahydro-5,5,8,8-tetramethyl-2-naphthyl)-6-benzo[b]thiophenecarboxylic acid, 6-[3-(1-adamantyl)-4-methoxyphenyl]-2-naphthanoic acid, or 6-[(3,4-dihydro 4,4-dimethyl-2H-1-benzothiopyran-6-yl)ethylnyl]-3-pyridinecarboxylic acid ethyl ester.

34. A method according to claim 23, wherein said retinoid is all-trans-retinoic acid; 13-cis-retinoic acid, 2-(5,6,7,8-tetrahydro-5,5,8,8-tetramethyl-2-naphthyl)-6-benzo[b]thiophenecarboxylic acid, 6-[3-(1-adamantyl)-4-methoxyphenyl]-2-naphthanoic acid, or 6-[(3,4-dihydro-4,4-dimethyl-2H-1-benzothiopyran-6-yl)ethylnyl]-3-pyridinecarboxylic acid ethyl ester.

* * * * *

UNITED STATES PATENT AND TRADEMARK OFFICE
CERTIFICATE OF CORRECTION

| | |
|---|---|
| PATENT NO. | : 7,083,799 B1 |
| APPLICATION NO. | : 08/894788 |
| DATED | : August 1, 2006 |
| INVENTOR(S) | : Paolo Giacomoni |

It is certified that error appears in the above-identified patent and that said Letters Patent is hereby corrected as shown below:

Column 12, line 7, delete colon after "B9".

Column 12, line 11, "alive agent" should read --active agent--.

Signed and Sealed this

Fifth Day of December, 2006

JON W. DUDAS
*Director of the United States Patent and Trademark Office*